United States Patent [19]

Solomon

[11] Patent Number: 5,229,108
[45] Date of Patent: Jul. 20, 1993

[54] PHARMACEUTICAL DOSAGE FORMS

[76] Inventor: Montague C. Solomon, 19 St. Leonards Terrace, London, United Kingdom, SW3

[21] Appl. No.: 789,931

[22] Filed: Nov. 12, 1991

[30] Foreign Application Priority Data

Nov. 20, 1990 [GB] United Kingdom ............... 9025251

[51] Int. Cl.⁵ ..................... A61K 9/16; A61K 9/22; A61K 9/36
[52] U.S. Cl. .................. 424/78.24; 424/474; 424/480; 424/489; 424/501; 424/464; 424/468
[58] Field of Search ............ 424/78.24, 489, 501, 424/464, 468

[56] References Cited

U.S. PATENT DOCUMENTS

| 4,167,558 | 9/1979 | Sheth et al. | 424/465 |
| 4,412,986 | 11/1983 | Kawata et al. | 424/80 |
| 4,499,066 | 2/1985 | Moro et al. | 424/465 |
| 4,562,069 | 12/1985 | Hegasy et al. | 424/497 |
| 4,778,816 | 10/1988 | Abe et al. | 514/381 |
| 4,880,623 | 11/1989 | Piergiorgio et al. | 424/465 |
| 4,882,144 | 11/1989 | Hegasy | 514/356 |
| 4,942,040 | 7/1990 | Ragnarsson et al. | 424/486 |
| 5,015,479 | 5/1991 | Mulligan et al. | 424/468 |

Primary Examiner—Thurman K. Page
Assistant Examiner—Amy Hulina
Attorney, Agent, or Firm—Kalish & Gilster

[57] ABSTRACT

Solid pharmaceutical slow release dosage forms of dihydropyridines such as nifedipine or nimodipine are manufactured by dissolving the dihydropyridine and polyvinylpyrollidone (PVP) in a solvent, adding colloidal silicon dioxide stepwise to the resultant viscous liquid until a granular mass is formed, drying the mass, and blending the product with an excipient.

14 Claims, No Drawings

PHARMACEUTICAL DOSAGE FORMS

TECHNICAL FIELD

The invention relates to solid dosage forms of dihydropyridines, for example nifedipine and nomidipine suitable for oral administration to human beings.

BACKGROUND ART

Nifedipine is the generic name for 4-(2'-nitrophenyl)-2, 6-dimethyl-3, 5-dicarbomethoxy-1, 4-dihydropyridine, an important vasodilator. It is light-sensitive and practically insoluble in water, so the preparation of formulations has been the subject of numerous Patent Specifications. Most have been concerned to achieve a rapid release of nifedipine into the blood stream. However, EP 47899 describes compositions containing crystals of particularly large surface area, which can be made into small tablets and give a long effective period but the preparation of such crystals is laborious. U.S. Pat. No. 4880623 describes sustained release compositions prepared by a lengthy, involved process productive of weighty tablets. Nomidipine is a similar medicine.

THE INVENTION

The invention provides a method of manufacturing a dosage form of a dihydropyridine which comprises dissolving the dihydropyridine and polyvinylpyrrolidone (PVP) in a solvent, adding colloidal silicon dioxide stepwise to the resultant viscous solution until a granular mass is formed, drying the mass, and blending the product with an excipient.

The method gives a slow release solid dosage form of the medicine with a uniform active compound content. This releases the active substance at a controlled rate so that the amount available in the body is maintained at a relatively constant level over an extended period of time. The method takes into account the interaction of the active dihydropyridine with the excipients, their quantities and formulation. It is not readily possible to predict whether a formulation will provide the desired sustained release effect.

A co-precipitate of the dihydropyridine and PVP in intimate mixture with the excipient is formed. The resultant granulate is preferably screened via an oscillating sieve and blended with sodium starch glycollate and cross-linked polyvinylpyrollidone (PVPP) as an excipient together with a lubricant, for example magnesium stearate. The product is put up in desired solid dosage form, preferably film-coated tablets.

In vitro dissolution tests surprisingly revealed that the release of nifedipine from the sustained release tablet formulation may be accelerated or retarded by varying the ratio of sodium starch glycollate to PVPP: more of the former slows the release rate. A similar but less marked effect may be obtained by increasing the proportion of PVP in the solution evaporated as this reduces the particle size in the co-precipitate.

The method of preparation is easy and economical to operate and can lead to a solid sustained release dosage form as shown by in vitro dissolution.

The colloidal (or fumed) silicon dioxide may be of a suitable grade of Aerosil (TM) or Syloid (TM) for example. The PVP may have a mean molecular weight of 10,000 to 50,000. The PVPP [Kollidon CL (TM)] has an indeterminate molecular weight due to its insolubility. It is a cross-linked insoluble polyvinylpyrollidone such as Polyplasdone XL (TM) from GAF, New York, N.Y., USA, or Kollidon CL (TM) from BASF, Ludwigshafen, Germany.

The following may preferably be used as solvents: a $C_1$ to $C_3$ alkanol; a $C_1$ or $C_2$—dialkylketone; or chlorinated alkane having 1 or 2 carbon atoms in the molecule. Specific examples include ethanol, acetone, methylene dichloride and chloroform, and mixtures of these solvents, but methylene dichloride is preferred. The solvent employed in an amount of from 4 to 8 parts by weight relative to the dihydropyridine.

The final blend may be tabletted and may be film-coated in conventional manner with hydroxypropylmethylcellulose and ethylcellulose. A colorant may be incorporated in the coating solution which may be either organic or aqueous.

EXAMPLE

A. QUANTITIES

| | |
|---|---|
| Nifedipine | 100 g (23.53%) |
| PVP (MW 29,000 Kollidon TM K25 Grade | 150 g (35.29%) |
| Methylene dichloride (solvent) | 40 ml |
| Colloidal Silicon Dioxide (Syloid TM 244FP grade) | 125 g (29.41%) |
| Sodium Starch Glycollate (disintegration agent) (Primogel TM) | 0.766 g (2.25%) |
| Cross-linked PVPP (Kollidon CL TM) | 3.064 g (9.00%) |
| Magnesium stearate lubricant | 0.170 g (0.50%) |
| Total | 379 g (99.99%) |

B. TECHNIQUE

The nifedipine (micronised to facilitate solvation) and PVP are dissolved in the methylene dichloride in a darkened room to avoid photo degradation of the nifedipine. The silicon dioxide is added stepwise with vigorous stirring until a thick viscous solution is formed. This solution is trayed out and air dried at room temperature. The resulting granular mass is screened through a 30BS screen on an oscillating sifter and blended with the sodium starch glycollate, cross-linked polyvinylpyrollidone (PVPP) and magnesium stearate, all of which have first been screened through a BS60 screen on an oscillating sifter. This final blend is passed through a 0.5 mm screen on a comminuting mill before compressing into tablets on a single stroke Manesty 'E' machine using a round normal concave punch with a diameter of one quarter of an inch (about 6.35 mn). Tablets having the following characteristics are obtained:

| | |
|---|---|
| Nifedipine content: | 20 mg |
| Theoretical weight: | 83 mg |
| Hardness: | 4.5–6 Kp (determined by Heberlein strain gauge) |
| Disintegration Time: | 10 minutes |

I claim:

1. A method of manufacturing a dosage form of a dihydropyridine which comprises (a) dissolving the dihydropyridine and polyvinylpyrrolidone (PVP) in a solvent, (b) adding colloidal silicon dioxide stepwise to the resultant visous liquid until a granular mass is formed, (c) drying the mass, and (d) blending the product with an excipient.

2. A method according to claim 1 in which the dihydroxypyridine is nifedipine.

3. A method according to claim 1 in which the dihydroxypyridine is nimodipine.

4. A method according to claim 1 in which the excipient is sodium starch glycollate, cross-linked polyvinylpyrollidone (PVPP) and a lubricant.

5. A method according to claim 1 in which there are used by weight 1 part of a dihydropyridine and from 1 to 4 parts of PVP having a mean molecular weight of from 10,000 to 50,000.

6. A method according to claim 4 in which there are used by weight 1 part of sodium starch glycollate and from 2 to 5 parts of PVPP.

7. A method according to claim 2 in which the excipient is sodium starch glycollate, cross-linked polyvinylpyrollidone (PVPP) and a lubricant.

8. A method according to claim 3 in which the excipient is sodium starch glycollate, cross-linked polyvinylpyrollidone (PVPP) and a lubricant.

9. A method according to claim 2 in which there are used by weight 1 part of a dihydropyridine and from 1 to 4 parts of PVP having a mean molecular weight of from 10,000 to 50,000.

10. A method according to claim 3 in which there are used by weight 1 part of a dihydropyridine and from 1 to 4 parts of PVP having a mean molecular weight of from 10,000 to 50,000.

11. A method according to claim 2 in which there are used by weight 1 part of sodium starch glycollate and from 2 to 5 parts of PVPP.

12. A method according to claim 3 in which there are used by weight 1 part of sodium starch glycollate and from 2 to 5 parts of PVPP.

13. A method according to claim 4 in which there are used by weight 1 part of a dihydropyridine and from 1 to 4 parts of PVP having a mean molecular weight of from 10,000 to 50,000.

14. A method according to claim 5 in which there are used by weight 1 part of sodium starch glycollate and from 2 to 5 parts of PVPP.

* * * * *